(12) United States Patent
Beumer

(10) Patent No.: US 8,394,855 B2
(45) Date of Patent: Mar. 12, 2013

(54) COSMETIC COMPOSITIONS

(75) Inventor: Raphael Beumer, Lörrach (DE)

(73) Assignee: DSM IP Assets B.V., Heerlen (NL)

( * ) Notice: Subject to any disclaimer, the term of this patent is extended or adjusted under 35 U.S.C. 154(b) by 12 days.

(21) Appl. No.: 13/137,659

(22) Filed: Sep. 1, 2011

(65) Prior Publication Data

US 2011/0312915 A1    Dec. 22, 2011

Related U.S. Application Data

(63) Continuation of application No. 11/990,490, filed as application No. PCT/EP2006/008961 on Sep. 14, 2006, now abandoned.

(30) Foreign Application Priority Data

Sep. 23, 2005  (EP) .................................. 05020779
Sep. 26, 2005  (EP) .................................. 05020905

(51) Int. Cl.
*A01N 37/00* (2006.01)
*A01N 25/00* (2006.01)
*A61K 31/20* (2006.01)
*A61K 47/00* (2006.01)

(52) U.S. Cl. ........................ 514/558; 514/784

(58) Field of Classification Search .................. 514/558
See application file for complete search history.

(56) References Cited

U.S. PATENT DOCUMENTS

| | | | |
|---|---|---|---|
| 5,057,501 A | 10/1991 | Thornfeldt | |
| 6,623,728 B2 | 9/2003 | Harichian et al. | |
| 2005/0171230 A1 | 8/2005 | Ishikawa et al. | |

FOREIGN PATENT DOCUMENTS

| DE | 2 312 280 | 9/1974 |
|---|---|---|
| DE | 103 07 387 A1 | 9/2004 |
| EP | 0 007 785 A2 | 2/1980 |
| EP | 0 442 708 A2 | 8/1991 |
| EP | 0 744 175 A2 | 11/1996 |
| EP | 1 249 236 A1 | 10/2002 |
| JP | 07223934 A | 8/1995 |
| WO | WO 98/13017 | 4/1998 |

OTHER PUBLICATIONS

International Search Report for PCT/EP2006/008961 mailed Dec. 28, 2006.
Ammon et al., "Inhibition of Colonic Water and Electrolyte Absorption by Fatty Acids in Man," *Gastroenterology* 65, pp. 744-749 (1973).
Jira et al (Strong increase in Hydroxy fatty acids derived fro linoleic acid in human low density lipoproteins of atherosclerotic patents; Chemistry and Physics of Lipids vol. 91, Issue 1, Jan. 1998, pp. 1-11).
Spitzer (Screening analysis of unknown seed oils Lipid (1999), vol. 101 Issue 1, pp. 2-19).

*Primary Examiner* — Sreeni Padmanabhan
*Assistant Examiner* — Layla Soroush
(74) *Attorney, Agent, or Firm* — Nixon & Vanderhye P.C.

(57) ABSTRACT

The present invention is concerned with novel cosmetic or pharmaceutical compositions. More particularly, the invention is concerned with novel cosmetic or pharmaceutical compositions for treating or preventing any symptoms caused by negative developments of the physiological homeostasis of healthy skin, as well as for the promotion of hair growth and protection from hair loss.

2 Claims, No Drawings

COSMETIC COMPOSITIONS

This application is a continuation of application Ser. No. 11/990,490 filed Feb. 15, 2008, now abandoned which in turn is the U.S. national phase of International Application No. PCT/EP2006/008961, filed 14 Sep. 2006, which designated the U.S. and claims priority to European Patent Application Nos. 05020779.4, filed 23 Sep. 2005, and 05020905.5, filed 26 Sep. 2005, the entire contents of each of which are hereby incorporated by reference.

The present invention is concerned with novel cosmetic or pharmaceutical compositions. More particularly, the invention is concerned with novel cosmetic or pharmaceutical compositions for treating or preventing any symptoms caused by negative developments of the physiological homeostasis of healthy skin, as well as for the promotion of hair growth and protection from hair loss.

Thus, in one aspect, the present invention is concerned with cosmetic or pharmaceutical compositions comprising a fatty acid containing 6 to 18 carbon atoms, which carries one or two hydroxyl, alkoxy, preferably methoxy or ethoxy, C2-C4-acylprotected amino, preferably C2, or oxo group, preferably between the positions C6 and C12; or a salt, ester or amide of such acids or a mixture of these acids; and a carrier conventionally used in cosmetic or pharmaceutical compositions.

The ester or amide are, preferably, an alkyl ester or alkyl amide, wherein the term "alkyl" encompasses straight chain as well as branched alkyl groups, i.e. that "$C_{1-4}$-alkyl" encompasses straight chain $C_{1-4}$-alkyl (methyl, ethyl, n-propyl, n-butyl) as well as branched $C_{3-4}$-alkyl (iso-propyl, iso-butyl, tert-butyl).

The salt may by formed by any cosmetically acceptable cation which means any metal cation as well as any organic cation that is not toxic to the skin and/or does not cause allergic reactions. Examples of such cations are ammonium salts and alkyl ammonium salts, alkali cations such as sodium and potassium ions and alkaline earth metal cations such as calcium and magnesium ions.

In one embodiment of the present invention the aliphatic fatty acid is a saturated straight-chain fatty acid or ω-branched-chain fatty acid which preferably has 6 to 18 carbon atoms. In another embodiment the aliphatic fatty acid is a saturated straight-chain or ω-branched chain fatty acid which has 6 to 18 carbon atoms and is substituted, preferably by hydroxy, between the positions C6 and C12. A particularly preferred fatty acid is 9-hydroxy stearic acid.

In a further aspect, the invention is concerned with cosmetic or pharmaceutical compositions comprising a fatty acid or a salt, ester or amide with the definitions and preferences as given above, and a retinoid.

Retinoids for use in the invention are, e.g., retinoic acid or retinol and isomers, e.g. 9-, 11- or 13-cis isomers thereof, and derivatives thereof which comprise retinyl esters such as the acetate, phenylbutyrate, propanoate, laurate, palmitate, oleate, linoleate; or retinyl alkyl carbonate; or ethers such as retinoxytrimethylsilane; or (all trans)-retinal or its acetals; or retinoic acid or amides thereof such as methoxy PEG-12 retinamide ("PEG-12" =—$(CH_2-CH_2-O-)_{12}$).

More specifically, the invention is concerned with cosmetic or pharmaceutical compositions comprising at least one fatty acid or a salt, ester or amide with the definitions and preferences as given above, and optionally one retinoid, for the treatment or prevention of symptoms caused by negative developments of the physiological homeostasis of healthy skin, as well as for the promotion of hair growth and protection from hair loss.

Treatment or prevention of symptoms caused by negative developments of the physiological homeostasis of healthy skin comprises treatment or prevention of wrinkles or dry skin or sensitive skin, thickening of the epidermis, inhibition of senescence of skin cells, prevention or treatment of photodamage, prevention or treatment of oxidative stress phenomena, prevention or treatment of cellulite, prevention and treatment of disturbances in ceramide and lipid synthesis, prevention of excess sebum production, reduction of activities of matrix metallo proteases or other proteases in the skin, treatment and prevention of inflammatory skin conditions including acne (=anti-acne), atopic eczema, polymorphic light eruption, psoriasis and vertiligo.

In still another aspect, the invention is concerned with a method of treatment or prevention of symptoms caused by negative developments of the physiological homeostasis of healthy skin as well as treatment or prevention of itchy or irritated skin and of promotion of hair growth and of protection from hair loss which method provides topically administering to a person in need of such treatment or prevention an effective amount of a fatty acid or a salt, ester or amide with the definitions and preferences as given above, optionally and preferably in combination with a retinoid and preferably in the form of a cosmetic or pharmaceutical composition according to the invention.

A preferred embodiment of the present invention is a method of treating or preventing wrinkles or human dry skin or sensitive skin, of promoting hair growth, of protecting from hair loss and of thickening the epidermis, which method comprises the step of topically administering to a person in need of such treatment or prevention an effective amount of a fatty acid or a salt, ester or amide with the definitions and preferences as given above, optionally and preferably in combination with a retinoid.

A further object of the present invention is a method for the prevention or treatment of pigmentation disorders and/or for providing an even skin tone, which method comprises the step of topically administering to a person in need of such prevention or treatment an effective amount of a composition according to the present invention as defined above, wherein the composition contains a retinoid.

Another object of the present invention is a method for fortifying the pigmentation which method comprises the step of topically administering to a person in need of such fortification an effective amount of a composition according to the present invention as defined above and topically administering a tanning active, wherein the tanning active may be administered before, after or simultaneously with the administration of the effective amount of the composition according to the present invention, and wherein any retinoid is essentially absent in such a composition.

The term 'an effective amount' refers to an amount necessary to obtain a physiological effect. The physiological effect may be achieved by one application dose or by repeated applications. The dosage administered may, of course, vary depending upon known factors, such as the physiological characteristics of the particular composition comprising the fatty acid or a salt, ester or amide with the definitions and preferences as given above, optionally in combination with a retinoid and its mode and route of administration; the age, health and weight of the recipient; the nature and extent of the symptoms; the kind of concurrent treatment; the frequency of treatment; and the effect desired and can be adjusted by a person skilled in the art.

In another embodiment, the compositions according to the present invention can be used for the treatment or prevention of symptoms caused by negative developments of the physiological homeostasis of healthy skin as defined above, as well as for the promotion of hair growth and protection from hair loss. The compositions according to the present invention can further be used for the treatment or prevention of itchy or irritated skin or for fortifying the pigmentation (the latter, however, only, if no retinoid but a tanning active is present.). If retinoid is, however, present in the composition of this invention the composition can be used for the prevention or treatment of pigmentation disorders and/or for providing an even skin tone, since the boosting of retinoids by the fatty acids or a salt, ester or amide thereof as defined above may lead to a depigmentation.

Preverably the compositions of the present invention are used for the treatment or prevention of wrinkles or dry skin or sensitive skin, for the promotion of hair growth, for the protection from hair loss, for thickening the epidermis, (if retinoid is present) for the prevention or treatment of pigmentation disorders and/or for providing an even skin tone, and/or (if retinoid is absent and a tanning active is present) for fortifying the pigmentation. Thus the composition according to the present invention, i.e. the fatty acids or a salt, ester or amide thereof with the definitions and preferences as defined above may fortify the pigmentation by enhancing the effect of a tanning active.

While, typically, the cosmetic or pharmaceutical compositions according to the present invention contain one of the fatty acids as defined above, the invention is not limited to that particular aspect and two or more fatty acids or a salt, ester or amide thereof as defined above may be present. As stated above, a retinoid may be additionally present, providing an additive or synergistic cosmetic effect, i.e. an improvement or prevention of symptoms caused by negative developments of the physiological homeostasis of healthy skin, as well as promotion of hair growth and protection from hair loss. Again, two or more retinoids may be present. If a retinoid is present in the compositions of the present invention, the ratio of the fatty acid or a salt, ester or amide with the definitions and preferences as given above) to the retinoid is suitably from about 1000:1 to 1:1000, more preferably from about 100:1 to 1:100 and in particular from about 30:1 to 1:30 by weight.

The fatty acids or a salt, ester or amide thereof as defined above show also an additive or synergistic effect with retinoids which are already present in the human skin.

In the compositions provided by the present invention, the amount of the fatty acid or a salt, ester or amide with the definitions and preferences as given above is suitably from about 0.0001 to about 50%, preferably from about 0.001 to about 20% by weight of the total composition. More preferably, the fatty acid as defined above are contained in the composition in an amount of about 0.01% by weight to about 1% by weight, most preferably in an amount of about 0.5% by weight. If a retinoid or derivative thereof is present, the amount of the latter is suitably from about 0.0001 to about 50% by weight, preferably from about 0.001 to about 20% by weight, most preferably in an amount of about 0.01 to about 1 weight %, in particular in an amount of about 0.1% by weight, based on the total amount of the composition. Preferred according to the invention is a composition comprising the fatty acid or a salt, ester or amide with the definitions and preferences as given above in an amount of about 0.5% by weight and a retinoid or derivative thereof in an amount of about 0.1% by weight, based on the total amount of the composition.

The term "cosmetic composition" as used herein e.g. refers to topical compositions for care of the human skin, see also the heading "Kosmetika" in Römpp Lexikon Chemie, 10th edition 1997, Georg Thieme Verlag Stuttgart, New York.

Regarding the kind of the topical (cosmetic or pharmaceutical) compositions and the preparation of the topical compositions as well as for further suitable additives, it can be referred to the pertinent literature, e.g. to Novak G. A., Die kosmetischen Präparate—Band 2, Die kosmetischen Präparate—Rezeptur, Rohstoffe, wissenschaftliche Grundlagen (Verlag für Chem. Industrie H. Ziolkowski K G, Augsburg).

The amount of the cosmetic or pharmaceutical composition according to the invention, which is to be applied to the skin depends on the concentration of the active ingredients in the compositions and the desired cosmetic or pharmaceutical effect. For example, application can be such that a crème is applied to the skin. A crème is usually applied in an amount of 2 mg creme/cm$^2$ skin. The amount of the composition which is applied to the skin is, however, not critical, and if with a certain amount of applied composition the desired effect cannot be achieved, a higher concentration of the active ingredients can be used e.g. by applying more of the composition or by applying compositions which contain more active ingredient.

The cosmetic or pharmaceutical composition according to the invention is preferably applied at least once per day, e.g. twice or three times a day. Usually it takes at least two weeks until the desired effect is achieved. However, it can take several weeks or even months until the desired effect is fully maximized.

The compositions of the present invention contain the fatty acids or a salt, ester or amide thereof with the definitions and preferences as defined above with cosmetically or pharmaceutically acceptable excipients or diluents. If nothing else is stated, the excipients, additives, diluents, etc. mentioned in the following are suitable for cosmetic compositions.

If nothing else is stated, in this application parts and percentages are per weight and are based on the total weight of the composition.

Preferably, the cosmetic or pharmaceutical compositions of the present invention are topical compositions in the form of a suspension or dispersion in solvents or fatty substances, or alternatively in the form of an emulsion or micro emulsion (in particular of O/W or W/O type, O/W/O or W/O/W-type), PET-emulsions, multiple emulsions, bickering emulsions, hydrogels, alcoholic gels, lipogels, one or multiphase solutions or a vesicular dispersion and other usual compositions, which can also be applied by pens, as masks or as sprays. The emulsions can also contain anionic, nonionic, cationic or amphoteric surfactant(s).

Preferred compositions according to the invention are skin care preparations, hair-care preparations, decorative preparations, light protection preparations and functional preparations.

Examples of skin care preparations are, in particular, body oils, body lotions, body gels, treatment creams, skin protection ointments, shaving preparations, such as shaving foams or gels, skin powders such as baby powder, moisturizing gels, moisturizing sprays, revitalizing body sprays, cellulite gels, anti acne preparations and peeling preparations.

Examples of hair care preparations are, for example, hair-washing preparations in the form of shampoos, hair conditioners, hair-care preparations, e. g. treatment preparations, pre-treatment preparations, hair tonics, styling creams, styling gels, pomades, hair rinses, treatment packs, intensive hair treatments, hair-straightening preparations, liquid hair-setting preparations, hair foams and hairsprays and lacquers, perming agents, hair gels, hair fixatives and hair dying or bleaching agents.

Examples of decorative preparations are in particular lipstick, eye shadow, mascaras, dry and moist make-up, rouge, powders, and suntan lotions.

Examples of functional preparations are cosmetic or pharmaceutical compositions containing active ingredients such as hormone preparations, vitamin preparations, vegetable extract preparations, anti-ageing preparations, and antimicrobial (antibacterial or antifungal) preparations without being limited thereto.

Cosmetic compositions in accordance with the invention can be in the form of a liquid, a lotion, a thickened lotion, a gel, a cream, a milk, an ointment, a paste, a powder, a make-up, or a solid tube stick and can be optionally be packaged as an aerosol and can be provided in the form of a mousse such as a aerosol mousse, a foam or a spray foams, sprays, sticks, a gel, a plaster, a powder, a cleanser, a soap or aerosols or wipes.

The compositions of the invention can also contain usual cosmetic or pharmaceutical adjuvants and additives, such as preservatives/ antioxidants, fatty substances/ oils, water, organic solvents, silicones, thickeners, softeners, emulsifiers, sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, e.g. those suited for providing a photoprotective effect by physically blocking out ultraviolet radiation, or any other ingredients usually formulated into cosmetics or medicaments.

An additional amount of antioxidants/ preservatives is generally preferred. Based on the invention all known antioxidants usually formulated into cosmetics or medicaments can be used. Especially preferred are antioxidants chosen from the group consisting of amino acids (e.g. glycine, histidine, tyrosine, tryptophane) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinsulfoximine, buthioninsulfone, penta-, hexa-, heptathioninsulfoximine) in very low compatible doses (e.g. pmol to μmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, Na-ascorbylacetate), tocopherol and derivatives (such as vitamin-E-acetate), mixtures of natural or synthetic vitamin E, vitamin A and derivatives (vitamin-A-palmitate and -acetate) as well as coniferylbenzoat, rutinic acid and derivatives, α-glycosylrutin, ferulic acid, furfurylidenglucitol, carnosine, butylhydroxytoluene, butylhydroxyanisole, trihydroxybutyrophenone, urea and its derivatives, mannose and derivatives, zinc and derivatives (e.g. ZnO, $ZnSO_4$), selenium and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount about 0.01 weight % to about 10 weight % of the total weight of the composition of the present invention. Preferably, one or more preservatives/antioxidants are present in an amount about 0.1 weight % to about 1 weight %.

Typically topical formulations also contain surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/ isostearic acid, polyglyceryl-6 hexaricinolate, polyglyceryl-4-oleate, polyglyceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glyceride phosphates and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount about 0.01 weight % to about 20 weight % of the total weight of the composition of the present invention. Preferably, about 0.1 weight % to about 10 weight % of emulsifiers is used.

The lipid phase of the topical compositions can advantageously be chosen from:
mineral oils and mineral waxes;
oils such as triglycerides of caprinic acid or caprylic acid and castor oil;
oils or waxes and other natural or synthetic oils, in a preferred embodiment esters of fatty acids with alcohols e.g. isopropanol, propylene glycol, glycerin or esters of fatty alcohols with carboxylic acids or fatty acids;
alkylbenzoates; and/or
silicone oils such as dimethylpolysiloxane, diethylpolysiloxane, diphenylpolysiloxane, cyclomethicones and mixtures thereof.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaureate, n-decyloleat, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the topical compositions of the present invention include polar oils such as lecithines and fatty acid triglycerides, namely triglycerol esters of saturated and/or unsaturated, straight or branched carboxylic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/ or branched hydrocarbons and waxes e.g. mineral oils, vaseline (petrolatum); paraffins, squalane and squalene, polyolefines, hydrogenated polyisobutenes and isohexadecanes, favored polyolefines are polydecenes; dialkyl ethers such as dicaprylylether; linear or cyclic silicone oils such as preferably cyclomethicones (octamethylcyclotetrasiloxane; cetyldimethicone, hexamethylcyclotrisiloxane, polydimethylsiloxane, poly(methylphenylsiloxane) and mixtures thereof.

Still other fatty components which can advantageously be incorporated in topical compositions of the present invention are isoeikosane; neopentylglykoldiheptanoate; propyleneglykoldicaprylate/dicaprate; caprylic/capric/diglycerylsuccinate; butyleneglycol caprylat/caprat; $C_{12-13}$-alkyllactate; di-$C_{12-13}$ alkyltartrate; triisostearin; dipentaerythrityl hexacaprylat/hexacaprate; propylenglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the compositions of the present invention can also contain natural vegetable or animal waxes such as bee wax, china wax, bumblebee wax and other waxes of insects as well as shea butter and cocoa butter.

A moisturizing agent may be incorporated into a topical composition of the present invention to maintain hydration or rehydrate the skin. Moisturizers that prevent water from evaporating from the skin by providing a protective coating are called emollients.

Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (ENJAY), diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 weight % to about 20 weight % of the total weight of the composition. The preferred amount of emollient is about 2 weight % to about 15 weight %, and most preferably about 4 weight % to about 10 weight %.

Moisturizers that bind water, thereby retaining it on the skin surface are called humectants. Suitable humectants can be incorporated into a topical composition of the present invention such as glycerin, polypropylene glycol, polyethylene glycol, lactic acid, pyrrolidon carboxylic acid, urea, phopholipids, collagen, elastin, ceramides, lecithin sorbitol, PEG-4, and mixtures thereof. Additional suitable moisturizers are polymeric moisturizers of the family of water soluble and/or swellable/ and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 weight % to about 8 weight % in a composition of the present invention, preferably about 1 weight % to about 5 weight %.

The aqueous phase of the preferred topical compositions of the present invention can contain the usual cosmetic or pharmaceutical additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or-monobutylether, diethyleneglycol monomethyl- or monoethylether and analogue products, polymers, foam stabilisators; electrolytes and especially one or more thickeners.

Thickeners that may be used in formulations of the present invention to assist in making the consistency of a product suitable include carbomer, siliciumdioxide, magnesium and/or aluminium silicates, beeswax, stearic acid, stearyl alcohol polysaccharides and their derivatives such as xanthan gum, hydroxypropyl cellulose, polyacrylamides, acrylate crosspolymers preferably a carbomer, such as carbopole® of type 980, 981, 1382, 2984, 5984 alone or mixtures thereof.

Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 weight % to about 8 weight % in the composition of the present invention, preferably, 1 weight % to about 5 weight %.

The addition of electrolytes into the composition of the present invention may be necessary to change the behavior of a hydrophobic emulsifier. Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 weight % to about 8 weight % in the composition of the present invention.

According to the invention for preparing the compositions of the invention the active ingredients can be used as such or in an encapsulated form, for example in a liposomal form. Liposomes are preferably formed with lecithins with or without addition of sterols or phytosterols. The encapsulation of the active ingredients can be alone or together with other active ingredients. It is possible to encapsulate only the fatty acid or a salt, ester or amide thereof with the preferences and definitions as defined above or only the retinoid, but it is also possible to encapsulate both ingredients either together or in separate capsules.

Other embodiments include solid or semisolid capsules aiming to protect the retinoid from degradation or for controlled delivery. The capsule may contain the retinoid alone or together with the fatty acid or a salt, ester or amide thereof with the preferences and definitions as defined above. Suitable encapsulation technologies are for example described in WO 0180823, WO 9903450, WO 9317784 or in Fragrance Journal (2001), 29(2), 83-90.

The composition of the present invention can also contain one or more additional pharmaceutically or cosmetically active ingredients, in particular for preventing or reducing acne, wrinkles, lines, atrophy, inflammation, as well as topical anesthetics, artificial tanning agents and accelerators, antimicrobial agents, antifungal agents and sun screening additives without being limited thereto.

Examples of such ingredients are peptides (e.g., Matrixyl™ [pentapeptide derivative]), oligopeptides, wax-based synthetic peptides (e.g., octyl palmitate and tribehenin and sorbitan isostearate and palmitoyl-oligopeptide), glycerol, urea, guanidine (e.g. amino guanidine); vitamins and derivatives thereof such as vitamin C (ascorbic acid), vitamin A (e.g., retinoid derivatives such as retinyl palmitate or retinyl propionate), vitamin E (e.g., tocopherol acetate), vitamin $B_3$ (e.g. niacinamide) and vitamin $B_5$ (e.g. panthenol), vitamin $B_6$ and vitamin $B_{12}$, biotin, folic acid; anti-acne actives or medicaments (e.g. resorcinol, salicylic acid, and the like); antioxidants (e.g. phytosterols, lipoic acid); flavonoids (e.g. isoflavones, phytoestrogens); skin soothing and healing agents such as aloe vera extract, allantoin and the like; agents suitable for aesthetic purposes such as essential oils, fragrances, skin sensates, opacifiers, aromatic compounds (e.g., clove oil, menthol, camphor, eucalyptus oil, and eugenol), desquamatory actives, hydroxy acids such as AHA acids, radical scavengers, farnesol, antifungal actives in particular bisabolol, alkyldiols such as 1,2-pentanediol, hexanediol or 1,2-octanediol, phytol, polyols such as phytanetriol, ceramides and pseudoceramides, amino acids, protein hydrolysates, polyunsaturated fatty acids, plant extracts like kinetin, DNA or RNA and their fragmentation products, carbohydrates, conjugated fatty acids, carnitin, carnosine, biochinonen, phytofluen, phytoen, and their corresponding derivatives.

Additionally the cosmetic and pharmaceutical topical composition of the present invention may contain UV-screening agents (UV-filter). The additional UV-screening agents are advantageously selected from IR, UV-A, UV-B, UV-C and/or broadband filters. Examples of UV-B or broad spectrum screening agents, i.e. substances having absorption maximums between about 290 nm and 340 nm may be organic or inorganic compounds. Organic UV-B or broadband screening agents are e.g. acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; Cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4, 2,2',4,4'-tetrahydroxybenzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene)propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as PARSOL® SLX; drometrizole trisiloxane (Mexoryl XL); imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like; salicylate derivatives such as isopropylbenzyl salicylate, benzyl salicylate, butyl salicylate, ethylhexyl salicylate (PARSOL® EHS, Neo Heliopan OS), isooctyl salicylate or homomenthyl salicylate (homosalate, PARSOL® HMS, Neo Heliopan HMS) and the like; triazine derivatives such as ethylhexyl triazone (Uvinul T-150), diethylhexyl butamido triazone (Uvasorb HEB) and the like. Encapsulated UV-filters such as encapsulated ethylhexyl methoxycinnamate (Eusolex UV-pearls) or microcapsules loaded with UV-filters as e.g. dislosed in EP 1471995 and the like;

Examples of broad spectrum or UV A screening agents i.e. substances having absorption maximums between about 320 nm and 400 nm may be organic or inorganic compounds. Organic broad spectrum or UV A screening agents include e.g. dibenzoylmethane derivatives such as 4-tert.-butyl-4'-methoxydibenzoyl-methane (PARSOL® 1789), dimethoxy-dibenzoylmethane, isopropyldibenzoylmethane and the like; benzotriazole derivatives such as 2,2'-methylene-bis-(6-(2H-benzotriazole-2-yl)-4-(1,1,3,3,-tetramethylbutyl)-phenol (Tinosorb M) and the like; bis-ethylhexyloxyphenol methoxyphenyl triazine (Tinosorb S) and the like; phenylene-1,4-bis-benzimidazolsulfonic acids or salts such as 2,2-(1,4-phenylene)bis-(1H-benzimidazol-4,6-disulfonic acid) (Neoheliopan AP); amino substituted hydroxybenzophenones such as 2-(4-Diethylamino-2-hydroxy-benzoyl)-benzoic acid hexylester (Uvinul A plus) as described in the European Patent Publication EP 1046391; Ionic UV-A filters as described in the International Patent Publication WO2005080341 A1; As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g. 3,3-Diphenylacrylate derivatives as described in the European Patent Publications EP 0 514 491 B1 and EP 0 780 119 A1; Benzylidene camphor derivatives as described in the U.S. Pat. No. 5,605,680; Organosiloxanes containing benzmalonate groups as described in the European Patent Publications EP 0358584 B1, EP 0538431 B1 and EP 0709080 A1.

A good overview of UV-A- and UV-B screening agents which can be added to the compositions of the present invention can also be found in DE-A 103 27 432. All UV-screening agents disclosed in this document are also useful as components for the compositions of the present invention and are included herein by reference. Additionally the composition of the present invention may contain UV-A and UV-B filters. Further examples of UV- filters or screening agents are disclosed, e.g., in WO 04/000256, see especially pages 10-12 which are included herein by reference.

A safe and effective amount of the UV-screening agent is used, typically from about 1 wt.-% to about 20 wt.-%, more typically from about 2 wt.-% to about 10 wt.-% based on the total weight of the composition.

Other suitable UV-screening agents which may be incorporated into the cosmetic or pharmaceutical topical compositions of the present invention are inorganic pigments such as microparticulated metal oxides (e.g. PARSOL® TX). Examples of such compounds include e.g. titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. The metal oxide particles may also be coated by metal oxides such as e.g. aluminum or zirconium oxides or by organic coatings such as e.g. polyols, methicone, aluminum stearate, alkyl silane. Such coatings are well known in the art. When used herein, the inorganic sunscreens are present in the amount of from about 0.1 wt.-% to about 20 wt.-%, preferably from about 0.5 wt.-% to about 10 wt.-%, more preferably from about 1wt.-% to about 5 wt.-% based on the total weight of the composition.

The fatty acids or a salt, ester or amide thereof with the preferences and definitions as given above are known or belong to a known class of compounds and as such can be prepared by known methods or in analogy thereto.

In another embodiment the invention relates to the use of a fatty acid or a salt, ester or amide with the definitions and preferences as given above for boosting the cosmetic effects of retinoids and/or tanning actives.

The efficacy of the compositions of the invention comprising fatty acid or a salt, ester or amide with the definitions and preferences as given above, optionally in combination with a retinoid as well as the concept of a synergistic effect between a retinoid and a fatty acid as defined above may be demonstrated in an in vitro test system using human primary keratinocytes as outlined below. The marker may be the enzyme Transglutaminase 1, which is a well-known and common differentiation marker in human epidermal cells.

Epidermal keratinocytes are isolated from human foreskin biopsies and cultured in keratinocyte serum free medium (KSFM, GIBCO) in a growth chamber with 37° C. and 5% $CO_2$. At the second passage, cells are transferred to 6 well plates and allowed to reach approximately 50% surface confluence.

The active ingredient(s) are solubilized in ethanol or ethanol/tetrahydrofuran. Retinoic acid solutions are handled under yellow light conditions only. When keratinocyte cultures reaches the appropriate confluence, the KSFM medium is supplemented with 1.3 mM calcium, in order to induce keratinocyte differentiation and thus also induce TG1 expression, and treatment is started by adding either a retinoid such as retinoic acid or a fatty acid or a salt, ester or amide with the definitions and preferences as given above or both substances in combination. For every sample, medium and/or treatment substances are changed twice daily. Seventy-two hours after the beginning of the treatment, cells are harvested and the RNA extracted. RNA is reverse transcribed into cDNA. Relative quantification of TG1 mRNA transcript levels in control versus treatment cultures are determined using multiplexed real time PCR analysis.

The ability of the cosmetic or pharmaceutical compositions of the present invention to reduce skin wrinkles may be assessed by profilometric methods described in "Skin topography measurement by interference fringe projection: a technical validation". (Lagarde J M; Rouvrais C; Black D; Diridollou S; Gall Y, Skin research and technology: official journal of International Society for Bioengineering and the Skin (ISBS) [and] International Society for Digital Imaging of Skin (ISDIS) [and] International Society for Skin Imaging (ISSI) (2001 May), 7(2), 112-21 or "Direct and non-direct measurement techniques for analysis of skin surface topography". Fischer T W; Wigger-Alberti W; Elsner P., Skin pharmacology and applied skin physiology (1999 January-April), 12(1-2), 1-11.

The ability of the compounds and compositions of the present invention to stimulate or protect hair growth may be determined with a mouse model described for example in WO 9817273. Instead of using Cyclophosphamide (Neostar, Pharmacia) to damage hair follicle Mitomycin, or Methotrexate can be used. It is also possible to detect hair growth acceleration with newborn mice. They have a synchronized hair cycle and approximately after 3 weeks all hair follicles go into the telogen phase. Then the animals are treated and it is evaluated how fast and to what extend the hair is growing Similar tests using in vitro or in vivo setups can also be found in J. Invest. Dermato. symposium proceedings 3rd Int. Meeting of Hair Research Societies, 8/1, p.39-45 (2003).

The following examples exemplify the invention, but they should not be construed as limiting the invention.

EXAMPLE 1

An anti-aging formulation containing the ingredients indicated below can be prepared in a manner known per se.

| Example formulation number 1 | |
| --- | --- |
| Ingredients | % (w/w) |
| Glyceryl Myristate | 4.00 |
| Cetyl Alcohol | 2.00 |
| Steareth-2 | 2.00 |
| Steareth-21 | 2.00 |
| Isopropyl Myristate | 5.00 |
| Tocopheryl Acetate | 0.50 |
| Ethylhexyl Methoxycinnamate | 4.00 |
| Ethylhexyl Salicylate | 2.00 |
| Butyl Methoxydibenzoylmethane | 1.00 |
| Almond Oil | 2.00 |
| BHT | 0.05 |
| Phenoxyethanol & Methylparaben & Ethylparaben & Propylparaben & Butylparaben & Isopropylparaben | 0.80 |
| Disodium EDTA | 0.10 |
| D-Panthenol | 0.30 |
| Propylene Glycol | 4.00 |
| Polyacrylamide & C13-14 Isoparaffin & Laureth-7 | 0.50 |
| 9-hydroxy stearic acid | 0.50 |
| Retinol 15D (Caprylic/Capric Triglyceride & Retinol) | 0.50 |
| Water | Ad 100 |
| Triethanolamine | q.s. |

EXAMPLE 2

An anti-aging formulations containing the ingredients indicated below can be prepared in a manner known per se.

| Example formulation number 2 | |
|---|---|
| Ingredients | % (w/w) |
| Glyceryl Myristate | 4.00 |
| Cetyl Alcohol | 2.00 |
| Steareth-2 | 2.00 |
| Steareth-21 | 2.00 |
| Isopropyl Myristate | 5.00 |
| Tocopheryl Acetate | 0.50 |
| Ethylhexyl Methoxycinnamate | 4.00 |
| Ethylhexyl Salicylate | 2.00 |
| Butyl Methoxydibenzoylmethane | 1.00 |
| Almond Oil | 2.00 |
| BHT | 0.05 |
| Phenoxyethanol & Methylparaben & Ethylparaben & Propylparaben & Butylparaben & Isopropylparaben | 0.80 |
| Disodium EDTA | 0.10 |
| D-Panthenol | 0.30 |
| Propylene Glycol | 4.00 |
| Polyacrylamide & C13-14 Isoparaffin & Laureth-7 | 0.50 |
| Water | Ad 100 |
| 9-hydroxy-stearic acid | 0.50 |
| Retinol Acetate 2.8 Ml | 0.10 |
| Triethanolamine | q.s. |

EXAMPLE 3

A facial treatment formulation containing the ingredients indicated below can be prepared in a manner known per se

| Formulation No. 3 | |
|---|---|
| Ingredients | % (w/w) |
| Glyceryl Myristate | 5.00 |
| Cetyl Alcohol | 2.00 |
| Cetyl Phosphate | 2.00 |
| Isopropyl Myristate | 10.00 |
| Tocopheryl Acetate | 0.30 |
| Almond Oil | 2.00 |
| BHT | 0.05 |
| Phenoxyethanol & Methylparaben & Ethylparaben & Propylparaben & Butylparaben & Isopropylparaben | 0.60 |
| Tromethamine | 0.90 |
| Water | Ad. 100 |
| D-Panthenol | 0.20 |
| Disodium EDTA | 0.10 |
| Propylene Glycol | 4.00 |
| Polyacrylamide & C13-14 Isoparaffin & Laureth-7 | 2.00 |
| 9-hydroxy stearic acid | 0.50 |
| Retinol 15D (Caprylic/Capric Triglyceride & Retinol) | 0.50 |
| Triethanolamine | q.s. |

EXAMPLE 4

A facial treatment formulation containing the ingredients indicated below can be prepared in a manner known per se

| Formulation No. 4 | |
|---|---|
| Ingredients | % (w/w) |
| Glyceryl Myristate | 5.00 |
| Cetyl Alcohol | 2.00 |
| Cetyl Phosphate | 2.00 |
| Isopropyl Myristate | 10.00 |
| Tocopheryl Acetate | 0.30 |
| Almond Oil | 2.00 |
| BHT | 0.05 |
| Phenoxyethanol & Methylparaben & Ethylparaben & Propylparaben & Butylparaben & Isopropylparaben | 0.60 |
| Tromethamine | 0.90 |
| Water | Ad. 100 |
| D-Panthenol | 0.20 |
| Disodium EDTA | 0.10 |
| Propylene Glycol | 4.00 |
| Polyacrylamide & C13-14 Isoparaffin & Laureth-7 | 2.00 |
| 9-hydroxy stearic acid | 0.50 |
| Retinol Acetate 2.8 Ml | 0.10 |
| Triethanolamine | q.s. |

EXAMPLE 5

Hair loss sera containing the ingredients indicated below can be prepared in a manner known per se

| Formulation No 5 | |
|---|---|
| Ingredients | % (w/w) |
| Water | Ad. 100 |
| Ethanol | 8.00 |
| Isopropanol | 4.00 |
| Propylene Glycol | 5.00 |
| D-Panthenol | 0.20 |
| PEG-12 Dimethicone | 0.20 |
| PEG-40 Hydrogenated Castor Oil | 4.00 |
| Phytantriol | 0.05 |
| Vitamin E Acetate | 0.10 |
| 9-hydroxy stearic acid | 0.50 |
| Retinol 15D (Caprylic/Capric Triglyceride & Retinol) | 0.50 |
| NaOH 10% | q.s. |

EXAMPLE 6

Hair loss sera containing the ingredients indicated below can be prepared in a manner known per se

| Formulation No 6 | |
|---|---|
| Ingredients | % (w/w) |
| Water | Ad. 100 |
| Ethanol | 8.00 |
| Isopropanol | 4.00 |
| Propylene Glycol | 5.00 |
| D-Panthenol | 0.20 |
| PEG-12 Dimethicone | 0.20 |
| PEG-40 Hydrogenated Castor Oil | 4.00 |
| Phytantriol | 0.05 |
| Vitamin E Acetate | 0.10 |
| 9-hydroxyy stearic acid | 0.50 |
| Retinol Acetate 2.8 Ml | 0.10 |
| NaOH 10% | q.s. |

EXAMPLE 7

A skin fortifier lotion containing the ingredients indicated below can be prepared in a manner known per se

| Formulation No. 7 | |
|---|---|
| Ingredients | % (w/w) |
| Water | Ad. 100 |
| D-Panthenol | 0.05 |
| Sodium Ascorbyl Phosphate | 0.20 |
| Propylene Glycol | 5.00 |
| Acrylates/C10-30 Alkyl Acrylate Crosspolymer | 0.50 |
| Sodium Hydroxide 30% | 0.40 |
| Disodium EDTA | 0.10 |
| Squalane | 2.00 |
| Phenoxyethanol & Methylparaben & Ethylparaben & Propylparaben & Butylparaben & Isopropylparaben | 0.80 |
| Coco-Caprylate/Caprate | 4.00 |
| BHT | 0.05 |
| Tocopheryl Acetate | 0.10 |
| Cyclomethicone | 3.00 |
| Glycerin | 3.00 |
| 9-hydroxy stearic acid | 0.50 |
| Retinol 15D (Caprylic/Capric Triglyceride & Retinol) | 0.50 |
| Sodium Hydroxide 10% | q.s. |

EXAMPLE 8

A skin fortifier lotion containing the ingredients indicated below can be prepared in a manner known per se

| Formulation No. 8 | |
|---|---|
| Ingredients | % (w/w) |
| Water | Ad. 100 |
| D-Panthenol | 0.05 |
| Sodium Ascorbyl Phosphate | 0.20 |
| Propylene Glycol | 5.00 |
| Acrylates/C10-30 Alkyl Acrylate Crosspolymer | 0.50 |
| Sodium Hydroxide 30% | 0.40 |
| Disodium EDTA | 0.10 |
| Squalane | 2.00 |
| Phenoxyethanol & Methylparaben & Ethylparaben & Propylparaben & Butylparaben & Isopropylparaben | 0.80 |
| Coco-Caprylate/Caprate | 4.00 |
| BHT | 0.05 |
| Tocopheryl Acetate | 0.10 |
| Cyclomethicone | 3.00 |
| Glycerin | 3.00 |
| 9-hydroxy stearic acid | 0.50 |
| Retinol Acetate 2.8 Ml | 0.10 |
| Sodium Hydroxide 10% | q.s. |

EXAMPLE 9

A formulation to treat age spots containing the ingredients indicated below can be prepared in a manner known per se

| Formulation No. 9 | |
|---|---|
| Ingredients | % (w/w) |
| Water | Ad. 100 |
| Polyquaternium-10 | 0.10 |
| D-Panthenol | 0.50 |
| Sodium Ascorbyl Phosphate | 1.00 |
| Niacinamid | 0.50 |
| Propylene Glycol | 4.00 |
| Glycerin | 3.00 |
| PEG-12 Dimethicone | 0.20 |
| Disodium EDTA | 0.10 |
| Polysorbate 20 | 5.00 |
| Phenoxyethanol & Methylparaben & Ethylparaben & Propylparaben & Butylparaben & Isopropylparaben | 0.80 |
| 9-hydroxy stearic acid | 0.50 |
| Retinol 15D (Caprylic/Capric Triglyceride & Retinol) | 0.50 |
| Sodium Hydroxide 10% | q.s. |

EXAMPLE 10

A formulation to treat age spots containing the ingredients indicated below can be prepared in a manner known per se

| Formulation No. 10 | |
|---|---|
| Ingredients | % (w/w) |
| Water | Ad. 100. |
| Polyquaternium-10 | 0.10 |
| D-Panthenol | 0.50 |
| Sodium Ascorbyl Phosphate | 1.00 |
| Niacinamid | 0.50 |
| Propylene Glycol | 4.00 |
| Glycerin | 3.00 |
| PEG-12 Dimethicone | 0.20 |
| Disodium EDTA | 0.10 |
| Polysorbate 20 | 5.00 |
| Phenoxyethanol & Methylparaben & Ethylparaben & Propylparaben & Butylparaben & Isopropylparaben | 0.80 |
| 9-hydroxy stearic acid | 0.50 |
| Retinol Acetate 2.8 Ml | 0.10 |
| Sodium Hydroxide 10% | q.s. |

EXAMPLE 11

Anti-cellulite formulations containing the ingredients indicated below can be prepared in a manner known per se

| Formulation No. 11 | |
|---|---|
| Ingredients | % (w/w) |
| Water | Ad. 100 |
| Caffeine | 1.00 |
| D-Panthenol | 0.50 |
| Glycerin | 4.00 |
| Butylene Glycol | 2.00 |
| Acrylates/C10-30 Alkyl Acrylate Crosspolymer | 0.20 |
| Disodium EDETA | 0.10 |
| Arachidyl Alcohol & Behenyl Alcohol & Arachidyl Glucoside | 5.00 |
| Squalane | 2.00 |
| Mineral Oil | 4.00 |
| Phenoxyethanol & Methylparaben & Ethylparaben & Propylparaben & Butylparaben & Isopropylparaben | 0.80 |
| Isononyl Isononanoate | 4.00 |
| BHT | 0.05 |
| Cetyl Alcohol | 2.00 |
| Dimethicone | 0.50 |
| Tocopheryl Acetate | 0.10 |
| 9-hydroxy stearic acid | 0.50 |
| Retinol 15D (Caprylic/Capric Triglyceride & Retinol) | 0.50 |
| Triethanolamine | q.s. |

EXAMPLE 12

An anti-cellulite formulation containing the ingredients indicated below can be prepared in a manner known per se

| Formulation No. 12 | |
|---|---|
| Ingredients | % (w/w) |
| Water | Ad. 100 |
| Caffeine | 1.00 |
| D-Panthenol | 0.50 |
| Glycerin | 4.00 |
| Butylene Glycol | 2.00 |
| Acrylates/C10-30 Alkyl Acrylate Crosspolymer | 0.20 |
| Disodium EDETA | 0.10 |
| Arachidyl Alcohol & Behenyl Alcohol & Arachidyl Glucoside | 5.00 |
| Squalane | 2.00 |
| Mineral Oil | 4.00 |
| Phenoxyethanol & Methylparaben & Ethylparaben & Propylparaben & Butylparaben & Isopropylparaben | 0.80 |
| Isononyl Isononanoate | 4.00 |
| BHT | 0.05 |
| Cetyl Alcohol | 2.00 |
| Dimethicone | 0.50 |
| Tocopheryl Acetate | 0.10 |
| 9-hydroxy stearic acid | 0.50 |
| Retinol Acetate 2.8 Ml | 0.10 |
| Triethanolamine | q.s. |

EXAMPLE 13

A skin repair formulation containing the ingredients indicated below can be prepared in a manner known per se

| Formulation No. 13 | |
|---|---|
| Ingredients | % (w/w) |
| Polyglyceryl-2 Dipolyhydroxystearate | 4.00 |
| Polyglyceryl-3 Diisostearate | 2.00 |
| Beeswax | 2.00 |
| Zinc Stearate | 2.00 |
| Caprylic/Capric Triglyceride | 3.00 |
| Cetearyl Isononanoate | 8.00 |
| Dicaprylyl Ether | 5.00 |
| BHT | 0.05 |
| Phenoxyethanol & Methylparaben & Ethylparaben & Propylparaben & Butylparaben & Isopropylparaben | 0.60 |
| Water | Ad. 100 |
| D-Panthenol | 0.20 |
| Disodium EDTA | 0.10 |
| Propylene Glycol | 4.00 |
| 9-hydroxy stearic acid | 0.55 |
| Retinol 15D (Caprylic/Capric Triglyceride & Retinol) | 0.50 |

EXAMPLE 14

A skin repair formulation containing the ingredients indicated below can be prepared in a manner known per se

| Formulation No. 14 | |
|---|---|
| Ingredients | % (w/w) |
| Polyglyceryl-2 Dipolyhydroxystearate | 4.00 |
| Polyglyceryl-3 Diisostearate | 2.00 |
| Beeswax | 2.00 |
| Zinc Stearate | 2.00 |
| Caprylic/Capric Triglyceride | 3.00 |
| Cetearyl Isononanoate | 8.00 |
| Dicaprylyl Ether | 5.00 |
| BHT | 0.05 |
| Phenoxyethanol & Methylparaben & Ethylparaben & Propylparaben & Butylparaben & Isopropylparaben | 0.60 |
| Water | Ad. 100 |
| D-Panthenol | 0.20 |
| Disodium EDTA | 0.10 |
| Propylene Glycol | 4.00 |
| 9-hydroxy stearic acid | 0.50 |
| Retinol Acetate 2.8 Ml | 0.10 |

What is claimed is:

1. A method of promotion of hair growth and of protection from hair loss, which consists of the step of topically administering to a person in need thereof an effective amount of a composition consisting of 9-hydroxystearic acid.

2. A method of promotion of hair growth and of protection from hair loss, which consists of the step of topically administering to a person in need thereof an effective amount of a composition consisting of 9-hydroxystearic acid in combination with a retinoid.

* * * * *